United States Patent [19]
Gordon et al.

[11] Patent Number: 5,398,539
[45] Date of Patent: Mar. 21, 1995

[54] CORRELATED MULTI-DIMENSIONAL CHROMATOGRAPHY WITH CONFIRMATORY HYBRID RUN

[75] Inventors: Gary B. Gordon, Saratoga; Bo U. Curry, Redwood City, both of Calif.

[73] Assignee: Hewlett-Packard Company, Palo Alto, Calif.

[21] Appl. No.: 101,322

[22] Filed: Aug. 2, 1993

[51] Int. Cl.$^6$ ............... G01N 30/02; B01D 15/08
[52] U.S. Cl. ............... 73/23.35; 73/23.39; 73/23.36; 73/61.53; 73/19.02; 210/656; 364/497; 422/70; 422/89; 436/161
[58] Field of Search ............ 364/497, 498; 73/23.39, 73/23.35, 23.36, 61.52, 61.53, 19.02; 422/70, 89; 436/161; 210/656, 198.2

[56] References Cited

U.S. PATENT DOCUMENTS

| | | | |
|---|---|---|---|
| 4,469,601 | 9/1984 | Beaver et al. | 210/658 |
| 4,592,842 | 6/1986 | Tomlinson | 422/70 X |
| 5,116,764 | 5/1992 | Annino et al. | 364/497 X |
| 5,196,039 | 3/1993 | Phillips et al. | 210/656 X |

OTHER PUBLICATIONS

J. B. Phillips et al., "Comprehensive Two Dimensional Gas Chromatography", May 13–16, 1991, vol. 1, 13th International Symposium on Capillary Chromatography, pp. 260–272.

J. B. Phillips et al., "High–Speed Two-Dimentional Gas Chromatography".

W. Jennings, "8.4 Multidimentional Chromatography", Analytical Gas Chromatography, 1987, pp. 170–174.

Primary Examiner—Robert J. Warden
Assistant Examiner—E. Leigh Dawson

[57] ABSTRACT

In a correlated two-dimensional gas chromatography system, it is necessary to "pair" peaks from one chromatogram with respective peaks of another chromatogram. Both peaks of a pair should correspond to the same sample component. The present invention provides for confirmation/disconfirmation of pairs that may be speculative or arbitrary. A hybrid chromatographic column is designed so that the retention time of a sample component is the average of the retention times of that component in the two independent columns. Thus, a peak location in the hybrid chromatogram can be calculated for each pair of peaks. The absence of a peak at that location or the inconsistency of the area of a peak at that location disconfirms the pairing. The invention also provides for higher dimensional systems and for other separation technologies.

9 Claims, 3 Drawing Sheets

CORRELATED MULTI-DIMENSIONAL CHROMATOGRAPHY WITH CONFIRMATORY HYBRID RUN

BACKGROUND OF THE INVENTION

The present invention relates to analytical chemistry and, more particularly, to correlated multidimensional chromatography. A major objective of the present invention is to provide for improved correlation of peaks from independent chromatographic separations of sample components.

Analytical chemistry has provided for fundamental advances in environmental and medical sciences. At the heart of analytical chemistry are techniques that provide for the separation, identification and quantification of components of a sample. "Chromatography" denotes a class of analytic methods that separate a sample into components as it moves along a separation path and typically provide for sequential quantification of the separated components. Herein, "chromatography" includes not only gas chromatography (GC) and liquid chromatography (LC), but also capillary electrophoresis (CE) and gel capillary electrophoresis (GCE).

In GC and LC, a sample is carried by a fluid (gas or liquid) that flows past a stationary support. As they flow past the support, some sample molecules are adsorbed to the support. The adsorption is reversible in that adsorbed sample molecules are desorbed to the fluid. Adsorbed sample molecules are considered to be in a "stationary phase", while desorbed molecules are considered to be in a "mobile phase".

As the number of adsorbed molecules increases, the rate of desorption increases until adsorption and desorption equalize. When equality is achieved, the proportions of each sample component in the mobile and stationary phases are in equilibrium. The partitioning of a component between the stationary phase and the mobile phase at equilibrium is a function of the component, the support material and the carrier fluid. For a given support material and carrier fluid, partitioning is a function of the sample components.

Sample components with a relatively large proportion of their molecules in the stationary phase, spend relatively less time in the mobile phase. Therefore, the migration rates for such components are less than the migration rates for sample components with relatively small proportions of their molecules in the stationary phase. It is this difference in migration rates that effects liquid and gas chromatographic separations.

In CE, an electric field is applied along a separation path. The electric field propels molecules in proportion to their charge, while viscous drag counters the propulsion in relation to the molecules size. Thus, CE separates sample components according to their charge-to-mobility ratios.

A detector, for example a thermal conductivity detector (for GC) or an ultraviolet absorption detector (for LC or CE), provides a time-varying output as separated sample components exit the solid phase. This time-varying output corresponds to the spatial distribution of the concentrations of the separated sample components. The time varying output can be recorded, providing a spatial representation of the spatial distribution of concentrations. The recorded output is referred to as a chromatogram. A typical chromatogram has a series of peaks. Each peak corresponds to a component band, or a group of unresolved component bands. Areas under peaks can be used to quantify the components.

One of the challenges of chromatography is to identify the sample component associated with a peak. Under carefully controlled conditions, sample components can be identified by the "retention time" at which they are detected. Test runs can be used to construct a table of retention times for expected analytes separated under specified conditions. One can then work backward from the retention time of a peak to determine the associated component. This identification approach is limited by the fact that many chemical moieties can have similar retention times. Furthermore, slight variations in conditions can cause retention times to vary. Providing tolerances for this variation greatly expands the number of chemical moieties that could correspond to a given retention time.

Identification can proceed much more surely by isolating the separated components and applying some well established identification technique. For example, GC/MS systems (gas chromatography/mass spectroscopy) systems separate components using gas chromatography and identify them using mass spectroscopy. Alternative identification techniques involve capturing eluting bands in separate vials. Various spectrographic and chemical tests can be applied to identify the component associated with the separated band. However, such physical isolation of separated components can be cumbersome when hundreds of peaks are involved.

In a "hyphenated" system, the step of collecting separate components can be avoided by appending a "fast" column to the end of a "slow" column. For example, a "fast" CE column can be abutted to the end of a "slow" LC column. The effluent of the slow column is sampled; the resulting sample slices are then run through,the fast column before the next slice enters the fast column. A single detector at the end of the fast column in effect identifies: 1) a "gross retention time" associated with the slice in which 1.5 a peak is detected, and thus the retention time in the slow column; and 2) a "fine retention time" the peak spent in the fast column. This permits two retention times to be associated with each band. Assuming the selectivity characteristics of the fast and slow column are different, the second retention time can be used to separate some chemical species that could not be separated on the basis of the first retention time alone. Thus, the chances of a unique identification are increased.

In practice, the slow and fast columns must be operated non-optimally in order to work well together. The resolutions of each are impaired by the need to infrequently sample from the slow column and drastically speed up the elution rate for the fast column. The lower resolutions broaden the peaks, causing severe overlaps and reducing the precision of identifications. Furthermore, sensitivities are limited because of the small sample sizes required for the fast column, which, of necessity, is usually small.

Correlated two-dimensional chromatography can enhance the identification capabilities of chromatography without requiring further analysis of separated components. In correlated two-dimensional chromatography, two columns of different selectivities are used. Two allotments of a sample are run respectively through the two columns. The runs are designed to be independent so that conditions can be optimized for each column. In practice, the runs can be concurrent to minimize analysis time. Generally, substances that are unresolved in one column can be resolved in the other. The results of each chromatogram can be used to confirm determinations based on the other chromatogram.

Correlated multi-dimensional chromatography is the generalization of this approach to two or more columns with different selectivities. Since runs are performed independently, each run can be optimized individually for resolution and speed. This provides a major advantage over the hyphenated approach in which resolution in each column is compromised so that fast column can separate the components in each sample slice within one sampling duration. Thus, a major advantage of this approach over the hyphenated approach is that both runs can be individually optimized for high sensitivity and high speed.

The challenge of correlated multidimensional chromatography is "correlating" peaks in two or more chromatograms. "Correlating" involves assigning a correspondence among peaks presumed to represent the same sample component. It can be difficult to determine which peak of one chromatogram corresponds with a given peak of the another chromatogram. Once the correct assignment is made, one can work backwards from tables of retention times for both runs to identify the component. To the extent that the selectivities for the runs are independent, the information on common-component peaks is generally much less ambiguous than the information from a single peak.

Unfortunately, it can be very difficult to determine which peaks are to be commonly assigned. For example, if there are 100 peaks in each of two chromatograms, there are 100! possible sets of peak pairings, assuming that the same 100 components are represented in each chromatogram. The number of possible correlations can be larger when overlapping is considered. Correlation techniques typically involve methods for excluding possible correlations, with an objective of being left with a single correlation. Many of "incorrect" correlations can be eliminated by comparing areas under peaks. This approach is limited by the usual presence of overlapping component bands that generate convolved peaks. Available knowledge about the sample can help exclude some possible correlations by the technique of training the particular apparatus on components expected to be present. However, this technique is not of use in correlating peaks for components not previously trained on. In some cases, however, there may be no basis for selecting among hundreds of possible correlations.

What is needed is a correlated multi-dimensional chromatographic method that provides for both high-resolution multi-dimensional separations and high-confidence co-assignment of peaks without requiring distinct identification procedures. More specifically, what is desired is a multi-dimensional separation method that provides for more accurate correlation of peaks across concentration distributions. Preferably, the method should work with a wide range of separation techniques.

SUMMARY OF THE INVENTION

The present invention provides a correlated multi-dimensional chromatography system with a plurality of independent separation paths and at least one confirmatory hybrid separation path. The method of the present invention involves sample runs through each of the independent and hybrid separation paths. Detectors associated with each of the separation paths provide chromatograms for the separation paths.

In a quite useful minimal configuration, the number N of independent separation paths is two, and the number M of confirmatory hybrid paths is one. For example, in such a case, a one-minute elution time from a first independent separation path and a three-minute elution time from a second independent separation path can be averaged to predict a two-minute elution time for a corresponding peak along a hybrid path. Additional confirmatory hybrid paths can increase the confidence of correlations. On the other hand, a single hybrid separation path can be economically used for more than two independent separations paths. In general, pairwise confirmation can be provided where $M=N(N-1)/2$, with greater Ms providing finer interpolations.

The independent separation paths are independent in the sense of "independent variable" in that the information in the resulting independent concentration distributions can be used to calculate estimated peak locations in the (dependent) hybrid concentration distribution. Preferably, the independent separation paths are also independent in that a component's location in one independent concentration distribution cannot be determined solely from its location in another concentration distribution. When the correlation among the independent concentration distributions is lower, the hybrid concentration distribution provides more useful confirmatory information.

Preferably, each hybrid separation path is constructed so that it is continuously characterized by a selectivity that is an average (weighted or unweighted) of the selectivities of two or more independent separation paths. For example, the hybrid path can have a stationary phase that is a mixture of the stationary phases used for the independent separation paths. Alternatively, the electric field of a CE separation path can be superimposed on a liquid chromatography column to yield a hybrid LC/CE separation path.

In some cases, for example, due to interactive effects, it is not feasible to combine selectivities in a continuous fashion. In such cases, a hybrid separation path can be constructed by abutting segments, each having a selectivity matched with one of the independent separation paths. In a two-dimensional case, only two segments need be used. Higher dimensions can be accommodated using more segments. Alternatively, segments can be arranged in a repeating pattern. A separation path with a repeating pattern of selectivities is particularly useful where gradient techniques are involved.

In the method of the present invention, sample allotments are run through the independent separation and the hybrid separation paths. A concentration distribution is obtained for each path run. Each peak observed in each concentration distribution represents one or more components of the original sample mixture; each such component contributes to exactly one peak in each separation path.

The present invention contributes additional constraints that can be used for disconfirming, i.e., excluding "incorrect", correlations between peaks from different separation runs. The additional constraints can be used exclusively or in combination with other constraints to exclude some or all incorrect correlations. The correlation technique can be applied to the set of all possible correlations, or to a subset derived using conventional constraints (e.g., peak areas). Using sophisticated statistical techniques, error values can be assigned to each correlation under consideration. In some cases, such techniques may identify a "best" correlation, or a group of best correlations. Such techniques are considered as disconfirming correlations that fall below threshold.

For each correlation under consideration, an expected hybrid chromatogram can be determined by calculating expected peak locations for a given confirmatory hybrid path. For example, in an N=2, M=1 system, the expected peak location of a peak in the hybrid chromatogram can be the weighted average of the locations of the corresponding peaks in the independent chromatograms. The expected chromatogram can be compared with the actual chromatogram; this comparison can result in an error measurement. The error measurement can involve a sum of Euclidean distances between an expected peak and the nearest actual peak. Alternatively, to this error measurement can be added a sum of the squares of the deviations of peak intensities from the mean intensity of all peaks assigned to a component. An error measurement is thus assigned for each proposed correlation. Those with the lowest errors are the most likely to be correct. The correlation with the lowest error can be selected as correct. Alternatively, the error information can be used with other information about the peak areas, to prioritize assignments. This correlation can include correlation techniques. However, the present invention provides additional constraints to exclude some incorrect pairs.

The hybrid and independent analytical separations can be performed concurrently to maximize analytical throughput, and to provide for common ambient conditions. Alternatively, the steps of the invention can be ordered in different ways. Of course, proposed assignments and calculation of expected position occur after the independent separations, and the determination of a peak at an expected location and comparison of peak areas occur after both separations.

In a two-dimensional realization of the present invention, a first separation column has a first selectivity, a second separation column has a second selectivity, and a hybrid separation column has a selectivity that is a linear, or other well-defined, combination of said first and second selectivities. In some embodiments, this can be achieved by continuously applying a mixture of the stationary phases associated with the two selectivities. Alternatively, respective segments of the hybrid separation path can be allocated to the first and second selectivities. This can be done by preparing an upstream half of a column to have the first selectivity and a downstream half to have the second selectivity. Preferably, however, alternating segments of first and second selectivities are used to accommodate gradient analytical procedures.

The concentration distributions associated with the two independent separation columns can be depicted respectively along orthogonal axis of a two-dimensional plot. Greater numbers of dimensions can be handled analogously. The hybrid concentration distribution can be plotted along a line as a linear combination of the independent chromatograms. Proposed assignments comprise a pair of peaks, one from each orthogonal concentration distribution. The assignment can be disconfirmed if a line drawn between the pair of peaks does not extend through a peak from the hybrid concentration distribution or if an intersected peak has an area inconsistent with the areas of the independent peaks. Lack of a disconfirmation can be treated as a confirmation.

The present invention retains the advantages of multidimensional analytical separations in that all information required for identification can be obtained in concurrent runs. No further analysis of separated components is required. In contrast to conventional multidimensional chromatography, the present invention provides for confirmation of correlations without reference to a table of retention times for pretested chemical moieties or to peak areas. On the other hand, the present invention can make use of peak area comparisons and retention time tables and still provide more confident identifications. As a result, a system using gas chromatography alone can approach the identification capabilities of a gas-chromatography/mass spectroscopy system. These and other features and advantages of the present invention are apparent from the description below with reference to the following drawings.

DESCRIPTION OF THE PREFERRED EMBODIMENTS

Figure 1:
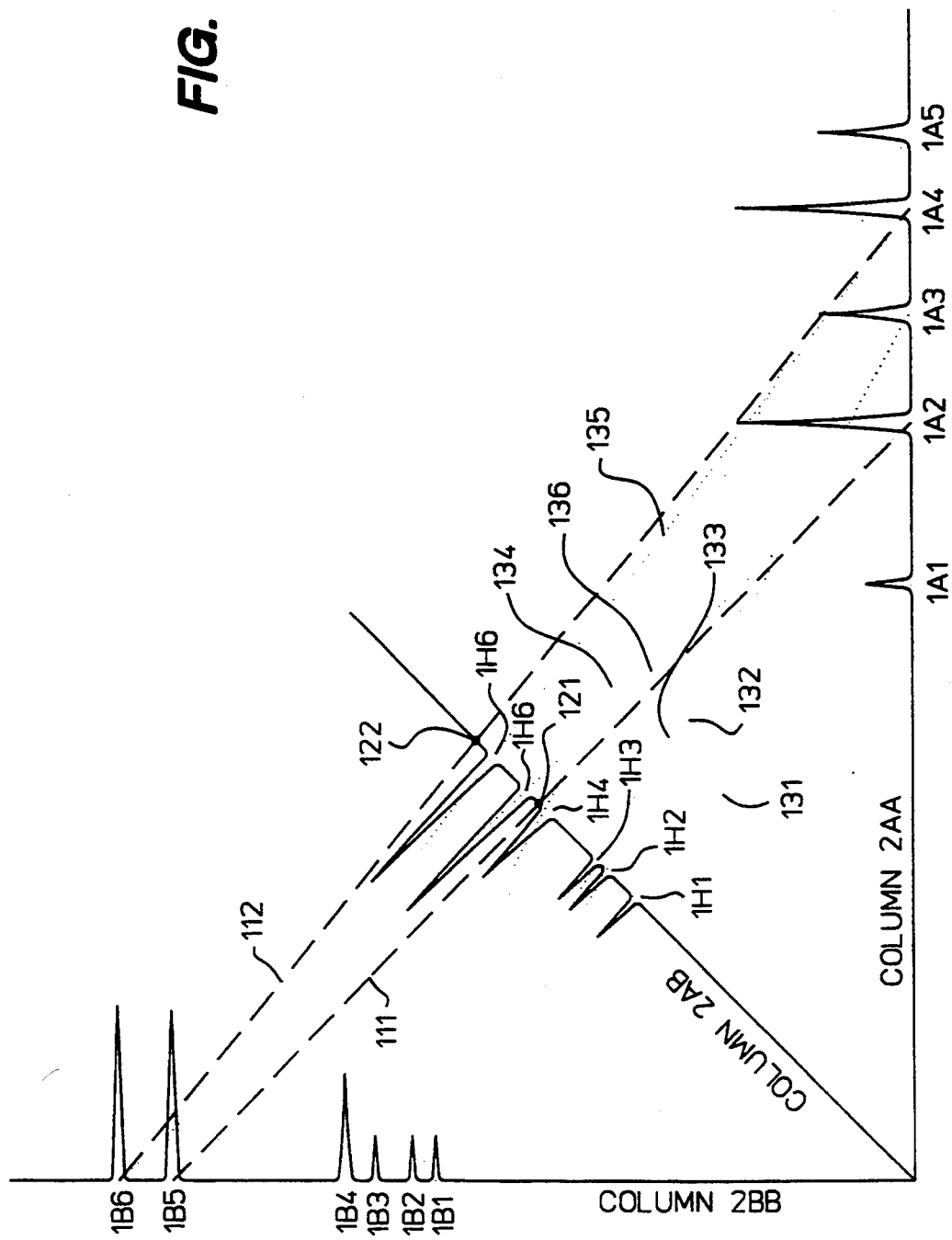
FIG. 1 is a two-dimensional concentration distribution obtained using a chromatography method flow-charted in FIG. 5 using the chromatography system illustrated in FIG. 2.
Figure 2:
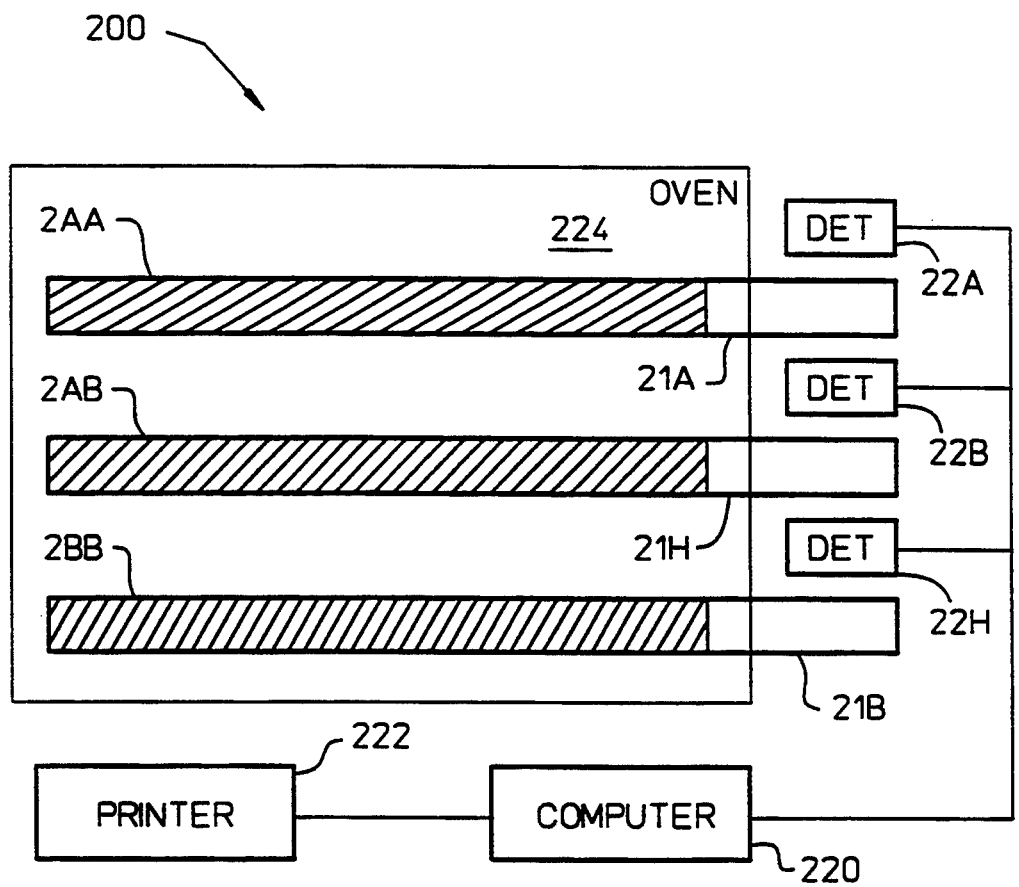
FIG. 2 is a two-dimensional gas analytical system in accordance with the present invention.

A two-dimensional concentration distribution, shown in FIG. 1, is produced using a two-dimensional gas chromatography system 200, shown in FIG. 2. System 200 includes a first independent separation column 2AA, a second independent separation column 2BB, a hybrid separation column 2AB, respective detection extensions 21A, 21B and 21H, detectors 22A, 22B and 22H, a computer 220, a printer 222, and an oven 224. Columns 2AA, 2BB and 2AB are disposed within oven 224, which provides precise control over column temperatures. Detection extensions 21A, 21B and 21H are disposed at the ends of respective separation columns 2AA, 2BB and 2AB for carrying elutents therefrom to respective detectors outside oven 224. Detectors 22A, 22B, and 22H are flame ionization detectors arranged for measuring the concentration of sequentially eluting sample components. The outputs of detectors 22A, 22B and 22H are coupled to computer 220. Computer 220 causes printer 222 to provide a hard copy representing the time-varying outputs of detects 22A, 22B and 22H. Computer 220 also controls column temperature by adjusting oven 224.

Separation columns 2AA and 2BB are independent in that their respective chromatograms can be used as independent variables to calculate estimate peak locations for the "dependent" hybrid separation column. In addition, columns 2AA and 2BB are selected so that there is a low magnitude of correlation of their outputs. This low magnitude correlation renders columns 2AA and 2BB independent in the sense that the retention time of an unidentified component eluting from column 2AA cannot be predicted from the retention time of the same component eluting from column 2BB, and vice-versa. For example, column 2AA might separate two components that column 2BB did not resolve, and column 2BB might separate two components that column 2AA did not resolve. One benefit of the low magnitude of correlation is that components unresolved in one column are relatively likely to be resolved on the other.

Column 2AB is dependent on columns 2AA and 2BB collectively, in that, if the retention times for columns 2AA and 2BB are known, the retention time in column 2AB can be calculated. More specifically, the solid phase for column 2AB is an equal parts mixture of the solid phases of columns 2AA and 2BB. The retention time in column 2AB is therefore the average of the retention times for a component in columns 2AA and 2BB.

Figure 3:
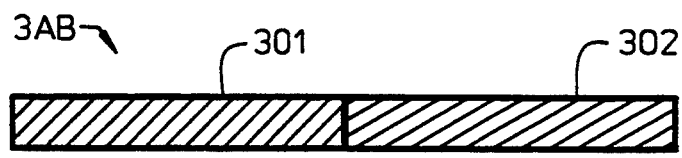
FIG. 3 is an alternative hybrid separation column employable in the system of FIG. 2.

In an alternative embodiment of the present invention, a hybrid column 3AB comprises two segments 301 and 302 as shown in FIG. 3. Segment 301 has the same stationary phase as column 2AA, while segment 302 has the same stationary phase has column 2BB. Segments 301 and 302 have equal lengths. Accordingly, for each component, the retention times for column 3AB are the average of respective retention times for columns 2AA and 2BB.

Figure 4:
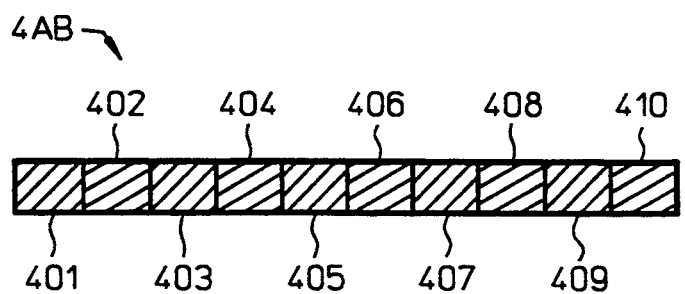
FIG. 4 is another alternative hybrid separation column employable in the system of FIG. 2.

Another alternative hybrid column 4AB includes ten segments 401-410, as shown in FIG. 4. Odd-numbered segments 401, 403, 405, 407, and 409 have the same stationary phase as column 2AA while even-numbered segments 402, 404, 406, 408, and 410 have the same stationary phase as column 2BB. Column 4AB is particularly useful where thermal gradient separations are employed but where it is not practical to mix the solid phases to achieve a continuous hybrid stationary phase.

Figure 5:
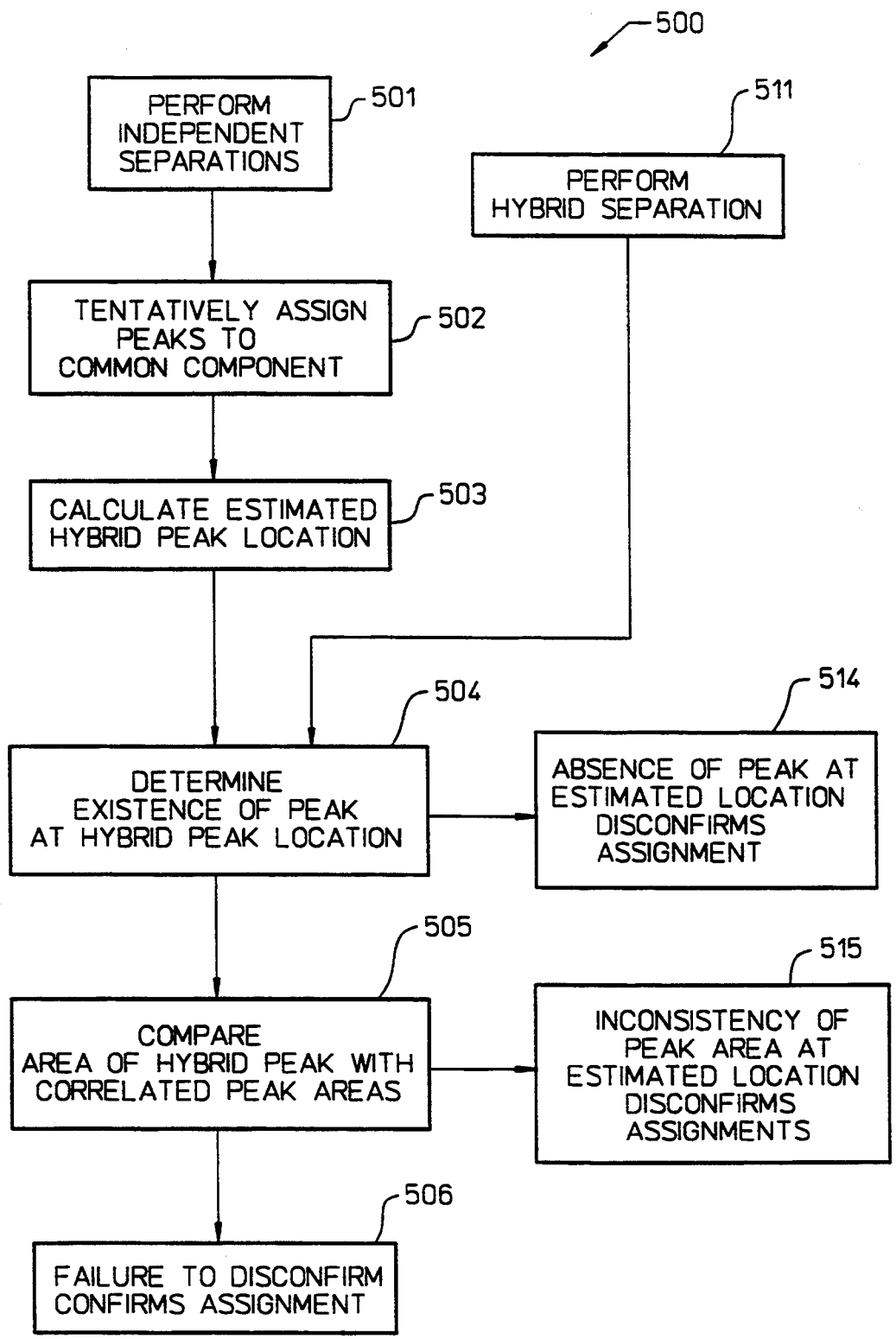
FIG. 5 is a flow chart of a method used with the system of FIG. 2 in accordance with the present invention to produce the two-dimensional concentration distribution of FIG. 1.

A method 500 employing component separation system 200 is flow charted in FIG. 5. Independent separation procedures are performed at step 501. The term "independent" is used in the "independent" vesus "dependent" sense in that the results of the independent separation procedures are used to calculate the results of a dependent separation procedure, which is termed "hybrid" herein. The term "independent" is also employed to connote orthogonality of the results of the independent separations procedures. Results are orthogonal when it is not possible to estimate the results of one independent separation procedure from the results of the other independent separations. Two strongly correlated separation procedures are not orthogonal. The present invention does not require that the independent separation procedures be or be proved orthogonal. However, greater orthogonality results in more useful information from the hybrid separation procedure.

Step 501 preferably involves concurrent runs to save analytical throughput and to ensure common conditions during a gradient run. Temporal, spatial, and spatiotemporal thermal gradients are provided for.

Step 502 involves assigning peaks to a common sample component. In other words, two peaks including one from each independent chromatogram are hypothesized to corresponding to a common component of the sample. The assignment can be completely arbitrary. For example, one could apply the disconfirmation procedure of the present invention to the full set of possible peak combinations. Preferably, some exclusions are done ahead of time to reduce numerical processing. The component need not be identified.

In step 503, the location in the hybrid chromatogram that the peak belonging to the common component would occupy given the hypothesized assignment is calculated. In the present embodiment, the location in the hybrid chromatogram would be half-way between the locations of the assigned peaks in their respective independent chromatograms. The calculation can yield a precise location or a location range to accommodate inter-run variations in retention times. In practice, a precise location can be calculated; the width of a peak can then define the tolerance for the center location of the peak.

A hybrid run is performed with the sample being separated along hybrid column 2AB, at step 511. Logically, this step is performed after the prediction of step 503 is made. In practice, this step is performed concurrently with step 501 to maximize analytical throughput. In addition, a concurrent run ensures that conditions are comparable across runs. This is particularly critical during gradient runs during which the temperature of oven 224 is ramped during component separation.

The hybrid chromatogram resulting from step 504 is examined for the presence of a peak at or within a tolerance of the location calculated in step 503. If there is no peak at or near the estimated location, the tentative assignment made in step 502 can be considered disconfirmed, as indicated at result 514.

If a peak is present at the estimated location, the areas of the assigned and hybrid peaks can be compared to find inconsistencies at step 505. If all components are separated, the peak areas for a given component should be comparable across runs. In some cases, a failure to separate can augment the area of one or more of the peaks. In some cases, an inconsistency cannot be explained by peak overlap. For example, if the areas of the independent assigned peaks are equal, this would counterindicate overlap; if the hybrid peak had lesser area than the two equal independent peaks, it would be unlikely that the hybrid peak represented the same peak as the independent peaks. Accordingly, the peak areas could be considered inconsistent and the assignment disconfirmed, as indicated at result 515. The confidence in this disconfirmation can be adjusted on the basis of other information. If the peak areas are the same or otherwise consistent, the failure of disconfirmation can be treated as a confirmation, as indicated at step 506.

Results of method 500 are illustrated in FIG. 1. Chromatograms 1AA, 1BB and 1AB, corresponding to the outputs of columns 2AA, 2BB and 2AB, are shown extending from a common origin. Chromatograms 1AA and 1BB are drawn along orthogonal axes, while chromatogram 1AB is drawn from a baseline directed at a 45° angle between chromatograms 1AA and 1BB. Chromatogram 1AA includes five peaks 1A1, 1A2, 1A3, 1A4 and 1A5. Chromatogram 1BB includes 6 peaks 1B1, 1B2, 1B3, 1B4, 1B5 and 1B6. The difference in the number of peaks (five versus six) suggests that two peaks of chromatogram 1AA are convolved. Comparison of peak areas suggest that the two largest peaks of chromatogram 1AA correspond to the same two components as do the largest two peaks of chromatogram 1BB. In other words, it is reasonable to propose that 1A2 and 1A4 correspond to the same components as 1B5 and 1B6. It is not clear whether 1A2 corresponds to 1B5 or to 1B6, and it is not clear whether IA4 corresponds to 1B5 or to 1B6.

Method 500 provides a basis for selecting one assignment as more probable than the other. Lines 111 and 112 represent proposed assignments of 1A2 to 1B5 and of 1A4 to 1B6. These lines 111 and 112 intersect chromatogram 1AB at points 121 and 122 respectively. Points 121 and 122 are not located at peaks, although 122 is close. Since the assignment of 1A4 to 1B6 is clearly disconfirmed, the assignment of 1A2 to 1B5 is also disconfirmed.

The alternative assignments of peak 1A4 to 1B5 and 1A2 to 1B6 is represented by lines 135 and 136. In addition, lines 131-136 and 111-112 represent a complete mapping of peaks 1B1-1B6 to peaks 1A1-1A5. Of note are lines 132 and 133 which respectively map both peaks 1B1 and 1B2 to peak 1A3. This pair of mappings indicates that peak 1A3 is a convolution of peaks corresponding to the components represented by peaks 1B2 and 1B3. This convolution is confirmed by peaks 1H2 and 1H3 on hybrid chromatogram 2AB, which are respectively intersected by lines 132 and 133. Note that peaks 1H2 and 1H3 are spaced apart about one half the distance that peaks 1B2 and 1B3 are, as would be expected if peak 1A3 represented unresolved sample components. This illustrates the effectiveness of method 500 in handling convolved peaks.

More sophisticated statistical disconfirmatory techniques can be used in place of or in addition to those described above. The following is presented as an illustrative disconfirmatory technique.

1) Correlations among peaks to components are tentatively proposed. In an exhaustive method, all possible correlations are considered. As discussed above, more efficient methods are generally available.
2) The expected position of a component peak on a hybrid separation path is predicted from the positions of peaks assumed to represent the same component in the respective independent separation paths. For example, linear interpolation can provide such a prediction.
3) An error or "cost" associated with each proposed correlation can be computed. For example, one can sum the Euclidean distance between observed and predicted peak positions, and then add the sum of the squares of the deviations of peak intensities from the mean intensity of all peaks assigned to a Component.
4) Selecting the lowest cost correlation.
5) Estimating the reliability of the lowest cost correlation, for example, by comparing the cost of the best correlation with the cost of the second best assignment.

While the present invention can be practiced with one confirmatory hybrid run for each pair of independent runs, in many cases finer interpolation can remove ambiguity in correlations. In the limiting case of continuous interpolation, one could "eye-ball" a correct correlation without ambiguity. In many cases, $N=2$, $M=3$, would provide confident correlations.

System 200 involves two-dimensional gas chromatography with a common thermal gradient. Those skilled in the art can see that the system and method can be extrapolated to three or more dimensions. Different thermal gradients can be applied by the independent separations, and an intermediate thermal gradient to the hybrid.

Separation technologies other than gas chromatography can be used. For example, the invention provides for separation by liquid chromatography, and electrophoresis. In the latter case, different pH buffers can be used for the independent columns and a buffer with an intermediate pH can be used for the hybrid column. The invention further applies where the independent separations are performed using different technologies. For example, the independent separations can involve liquid chromatography and capillary zone electrophoresis. The hybrid column supplies an electric field along a liquid chromatography column.

Other combinations of separation technologies can be employed. The key elements are the combinability of the techniques to yield a hybrid separation and a low-magnitude correlation of the separations achieved by the independent separations. These and other variations upon and modifications to the described embodiments are provided for by the present invention, the scope of which is limited only by the following claims.

What is claimed is:

1. A multidimensional chromatography method comprising the steps of:
    a) separating components of a sample according to N independent separation procedures and a hybrid separation procedure, N being an integer greater than unity,
        said N separation procedures resulting in N independent concentration distributions,
        said hybrid separation procedure resulting in an actual hybrid concentration distribution,
        each of said hybrid and independent concentration distributions including a respective series of peaks at respective locations within the respective distribution;
        said hybrid separation procedure being selected so that an estimated hybrid peak location for a respective one of said sample components can be calculated from the locations of N independent peaks, each from a respective one of said N independent concentration distributions and each corresponding to said respective sample component, said estimated hybrid peak location being calculable according to a function that varies with each of said N independent peak locations;
    b) proposing an assignment of N peaks from respective ones of said N independent concentration distributions to said sample component;
    c) calculating the estimated location of a confirming peak along said hybrid concentration distribution; and
    d) examining said hybrid concentration distribution for the presence of a confirming peak at said expected location;
    whereby, the absence of a confirming peak can disconfirm said proposed assignment of N peaks.

2. A method as recited in claim 1 further comprising a step of comparing the area of said confirming peak with the areas of said N peaks;
    whereby, a disconfirmation can result despite the presence of a peak at said estimated location when the area of said confirming peak is significantly less than the area of the peak of minimum area among those proposed for assignment in step b.

3. A method as recited in claim 1 wherein said hybrid separation procedure involves component separation along a path characterized by a continuous hybrid selectivity characteristic.

4. A method as recited in claim 1 wherein said N independent separation procedures include a first independent separation procedure in which said sample components are separated along a first independent separation path characterized by a first selectivity characteristic, said N independent separation procedures including a second independent separation procedure in which sample components are separated along a second independent separation path characterized by a second selectivity characteristic, said hybrid separation procedure involving separation of sample components along a hybrid separation path including a first segment characterized by said first selectivity characteristic and a second segment characterized by said second selectivity characteristic, said second segment being downstream of said first segment.

5. A method as recited in claim 4 wherein said hybrid separation path includes a third segment downstream of said second segment and characterized by said first selectivity characteristic.

6. A multidimensional chromatography system comprising:
   a) means fop separating components of a sample according to N independent separation procedures and a hybrid separation procedure, N being an integer greater than unity,
      said N separation procedures resulting in N independence concentrating distributions,
      said hybrid seperation procedure resulting in an actual hybrid concentration distribution,
      each of said hybrid and independent concentration distributions including a respective series of peaks at respective locations within the respective distribution;
      said hybrid separation procedure being selected so that an estimated hybrid peak location for a respective one of said sample components can be calculated from the locations of N independent peaks, each from a respective one of said N independent concentration distributions and each corresponding to said respective sample component, said estimated hybrid peak location being calculable according to a function that varies with each of said N independent peak locations;
   wherein said N independent separation procedures are characterized by N different selectivity characteristics, said N independent separation procedures including a first independent separation procedure characterized by a first selectivity characteristic and a second independent separation procedure characterized by a second selectivity characteristic, said second selectivity characteristic being different from said first selectivity characteristic and said hybrid separation procedure characterized by a hybrid selectivity characteristic, said hybrid selectivity characteristic being a combination of said N different selectivity characteristics;
   b) detector means for producing respective chromatograms of said concentration distributions for each of said independent and hybrid separation procedures;
   c) means for proposing an assignment of N peaks from respective ones of said N independent concentration distributions to said sample component;
   d) means for calculating the estimated location of a confirming peak along said hybrid concentration distribution; and
   e) means for examining said hybrid concentration distribution for the presence of a confirming peak at said expected location and for disconfirming said proposed assignment of N peaks in the absence of a confirming peak.

7. A system as recited in claim 6 wherein said hybrid separation path includes:
   a first segment characterized by said first selectivity characteristic; and a second segment characterized by said second selectivity characteristic; said second segment being downstream of said first segment.

8. A system as recited in claim 6 wherein said hybrid separation path includes a first group of segments characterized by said first selectivity characteristic, said hybrid path further including a second group of segments characterized by said second selectivity characteristic, segments of said first and second groups being mutually interposing.

9. A system as recited in claim 6 wherein said hybrid separation path is continuously characterized by said hybrid selectivity characteristic.

* * * * *